United States Patent
Xu et al.

(10) Patent No.: US 12,357,989 B2
(45) Date of Patent: Jul. 15, 2025

(54) CO-DETECTION AND DIGITAL QUANTIFICATION OF BIOASSAY

(71) Applicant: Zhejiang Dapu Biotechnology Co., Ltd., Zhejiang (CN)

(72) Inventors: Xiaonan Xu, Jieyang (CN); Ruyuan Song, Huanghua (CN); Shuhuai Yao, Hong Kong (CN); Kwok Fai Joseph Chow, Hong Kong (CN)

(73) Assignee: Zhejiang Dapu Biotechnology Co., Ltd., Jiaxing (CN)

( * ) Notice: Subject to any disclaimer, the term of this patent is extended or adjusted under 35 U.S.C. 154(b) by 1085 days.

(21) Appl. No.: 17/266,596

(22) PCT Filed: Aug. 26, 2019

(86) PCT No.: PCT/CN2019/102474
§ 371 (c)(1),
(2) Date: Feb. 7, 2021

(87) PCT Pub. No.: WO2020/043036
PCT Pub. Date: Mar. 5, 2020

(65) Prior Publication Data
US 2021/0308678 A1    Oct. 7, 2021

Related U.S. Application Data

(60) Provisional application No. 62/723,455, filed on Aug. 27, 2018.

(51) Int. Cl.
*B01L 3/00* (2006.01)
*C12Q 1/6806* (2018.01)
(Continued)

(52) U.S. Cl.
CPC ... *B01L 3/502753* (2013.01); *B01L 3/502784* (2013.01); *C12Q 1/6806* (2013.01); *C12Q 1/6851* (2013.01); *C12Q 1/703* (2013.01); *G01N 15/1459* (2013.01); *G01N 33/54366* (2013.01); *G01N 33/6803* (2013.01); *B01L 2200/0668* (2013.01); *B01L 2300/0893* (2013.01); *G01N 2015/003* (2013.01); *G01N 2015/1486* (2013.01)

(58) Field of Classification Search
None
See application file for complete search history.

(56) References Cited

U.S. PATENT DOCUMENTS

2016/0231324 A1* 8/2016 Zhao ............... G01N 33/57496
2016/0288121 A1* 10/2016 Ismagilov ............. C12Q 1/025
(Continued)

*Primary Examiner* — Lore R Jarrett
(74) *Attorney, Agent, or Firm* — NZ Carr Law Office

(57) ABSTRACT

The present invention provides methods and devices for detecting and quantifying multiple biomolecules at single-molecule level using an integrated droplet microfluidic system. In one embodiment, the present invention provides real-time and digital measurement of multiple biomolecules in a sample, thereby quantifying multiple biomolecules in an absolute and simultaneous manner. In one embodiment, the present invention provides a diagnostic method for a disease, comprising real-time and digital measurement of multiple biomolecules in a sample using the method or device described herein.

17 Claims, 6 Drawing Sheets

(51) Int. Cl.
  *C12Q 1/6851* (2018.01)
  *C12Q 1/70* (2006.01)
  *G01N 15/00* (2024.01)
  *G01N 15/14* (2024.01)
  *G01N 33/543* (2006.01)
  *G01N 33/68* (2006.01)

(56) References Cited

U.S. PATENT DOCUMENTS

2018/0147573 A1\* 5/2018 Hiddessen ............ B01F 33/813
2018/0250672 A1\* 9/2018 Jamshidi ............... C12Q 1/6806

\* cited by examiner

CO-DETECTION AND DIGITAL QUANTIFICATION OF BIOASSAY

CROSS REFERENCE TO RELATED APPLICATION

The present application claims priority of U.S. Patent provisional Application No. 62/723,455, filed on Aug. 27, 2018. The content of this application including all tables, diagrams and claims is incorporated hereby as reference in its entity.

FIELD OF THE INVENTION

The present invention relates to methods and devices for detecting and quantifying multiple biomolecules at single-molecule level using an integrated droplet microfluidic system.

BACKGROUND OF THE INVENTION

There are numerous biomarkers present in the human biofluids, such as blood, urine, saliva and seminal plasma. Circulating biomarkers present in blood include cell free DNA (cf DNA), protein, extracellular vesicles and circulating tumor cells. Accurate quantification of biomarkers is significant incorrect and reliable diagnosis, prognosis, and progression monitoring of diseases or conditions, in particular for detection of disease in its early stage or prenatal screening in the form of non-invasive prenatal testing (NIPT). However, at the time of this invention, the only widely used blood test for detection of early-stage prostate cancer is based on the measurement of prostate specific antigen (PSA) marker, and the proper use of this test is still controversial. To measure the quantity of the biomarkers with high sensitivity and specificity is of critical importance to prevent misdiagnosis because otherwise too many healthy individuals will receive false positive test results, leading to unnecessary follow-up procedures and anxiety, while in the other way around, false negative test results may lead to delay in treatment and adversely affect the patients. Also, from the aspect of scientific discovery, accurate quantification of biomarkers is important for understanding the correlation between biomarkers and corresponding disease and establishing a reliable and robust correlation for use as a clinical indicator of the disease.

Numerous efforts have been made in academia and industry to quantify different types of biomarkers. Traditional ways for nucleic acid quantification include analysis of bands of gel electrophoresis of products from polymerase chain reactions (PCR), real time PCR and recently emerging technologies such as next generation sequencing (NGS) and other sequencing methods. For protein quantification, enzyme-linked immunos or bent assay (ELISA) method has been widely used and protein mass spectrometry as recently emerged can also be used. For exosome quantification, nanoparticle tracking analysis (NTA) and ExoELISA™ method are widely adopted.

The methods mentioned above have been widely adopted in laboratories or clinics.

However, these methods cannot provide enough sensitivity for a valid and sensitive diagnosis or are not capable of absolute quantification and therefore are not competent for diagnostic tests that require the biomarkers be quantified with high precision for a valid result. At the time of this invention, most of the traditional diagnostic methods which require quantification of markers utilize bulk volume assay for markers quantification and can only give a qualitative or semi-quantitative result since the molecular information obtained is the average information of thousands of events of the bulk volume assay, thus the detection may not be very precise. On the other hand, new methods based on NGS or mass spectrometry (MS) enable a high throughput and accurate measurement of the markers but are relatively time consuming and expensive to implement. This is especially true when these methods generate a large amount of unnecessary data, complicating the post-data analysis.

Another important concern is that most of the current diagnostic platforms are not able to detect and/or quantify multiple biomarkers of different types such as DNA and protein markers simultaneously. Some diseases may require a co-detection of two or more markers for an accurate diagnosis. For example, clinical research has demonstrated that the maximum sensitivity of plasma DNA-based tests ("liquid biopsies") was limited to localized cancers. Combined detection of genetic alterations and protein biomarkers may not only help to identify the presence of relatively early cancers but also to localize the organ of origin of these cancers. Accuracy of the detection or diagnosis could be essentially improved since the test requires co-detection of multiple biomarkers and particular correlation among their levels in order to clinically establish the existence of a condition or disease.

In recent years, digital technology such as digital PCR and digital ELISA technology which use microfluidic technology to compartmentalize as ample into thousands of isolated aliquots has emerged. Thousands of PCR or ELISA reactions occur in the individual space without interference, thereby enabling the detection to be reduced to single molecule level and absolute and accurate quantification of biomolecules. It brings the molecular diagnostics to unprecedented accuracy while at the same time preserves the high specificity of the PCR and ELISA assays. However, current digital platforms are limited to end-point detection (i.e., detection after end of reactions) and one single type of reaction and detection (e.g., digital PCR reactions and digital ELISA reactions cannot be integrated into one platform such that PCR reactions and ELISA reactions can be carried out in different droplets). Therefore, these current digital platforms cannot detect multiple biomolecules in a real-time manner.

SUMMARY OF THE INVENTION

This invention introduces for the first time the concept of using a digital platform in microfluidic setting for co-detecting multiple biomolecules down to single molecule level and quantifying these multiple biomolecules in a real-time manner, thereby allowing an efficient and accurate diagnosis.

The present invention provides methods and devices for detecting and quantifying multiple biomolecules at single-molecule level using an integrated droplet microfluidic system.

In one embodiment, the present invention provides a real-time and digital measurement of multiple biomolecules in a sample, thereby quantifying multiple biomolecules in an absolute and simultaneous manner.

In one embodiment, the present invention provides a diagnostic method for a disease, comprising a real-time and digital measurement of multiple biomolecules in a sample using the method or device described herein.

In one embodiment of the present integrated droplet microfluidic system for digital quantification of bioassay, said system including four parts (from left to right): inlets, a droplet generator, a droplet storage chamber and an outlet. Inlets are used to introduce various liquids (e.g. oil, samples and reagents for carrying out reactions) to the droplet generator, wherein these liquids can be loaded separately through different inlets, or premixed and loaded as a mixture through the same inlet. Sample containing biomolecules is prepared and compartmentalized into isolated droplets through the droplet generator, the droplets generated are then spread in a one-layer configuration in a droplet storage chamber. After sample compartmentalization, parallel in situ reactions happen in individual droplets, where the reactions are part of a reaction assay for analyzing the target biomolecules, and the reactions in different droplets can be the same or different. Once the reactions are completed, signals indicating the presence of target biomolecules are detected by, for example, capturing the image of the droplets in the droplet storage chamber by a microscopic camera. The images are then processed by computer for digital counting and data analysis. Outlet is for removal of liquid or gas from the system. In one embodiment, outlet is for air or oil draining. In another embodiment where droplets need to be collected after reactions, they can be collected from the droplet storage chamber through the outlet.

In one embodiment, the present methods and devices comprise an integrated droplet microfluidic system which is capable of generating thousands of droplets, thereby compartmentalizing a sample into thousands of isolated droplets for subsequent reactions and analysis per single droplet.

In one embodiment, the present invention provides an integrated droplet microfluidic system for generating a plurality of isolated droplets from a sample.

In one embodiment, the present integrated droplet microfluidic system is configured as one single microfluidic chip.

In one embodiment, the present microfluidic system is formed by a droplet generator and a droplet storage chamber. In one embodiment, a sample containing biomolecules is compartmentalized into isolated droplets through a droplet generator, the droplets generated are then deposited in the droplet storage chamber in a one-layer configuration.

In one embodiment, the present integrated droplet microfluidic system comprises a plurality of microfluidic channels for delivering fluids to and from various components of the system. In one embodiment, the present droplet generator, droplet storage chamber and/or outlet comprises one or more microfluidic channels which set the flow paths of the fluids within these components. In one embodiment, one or more microfluidic channels are provided between different components of the integrated droplet microfluidic system (e.g. between droplet generator and droplet storage chamber) so as to direct fluid from one component to another component. In one embodiment, the exact type or configuration (e.g. structure, length, diameter, number of branches and density) of the microfluidic channels to be used depends on the purpose of having the microfluidic channels and the desirable flow resistance of individual components.

In one embodiment, the present invention enables real-time and digital measurement of multiple droplets generated from a sample by quantitative and independent measurement of a specific signal in each droplet.

In one embodiment, by utilizing the present integrated droplet microfluidic system coupled with a motion and temperature control system and a detection unit, the present invention is capable of conducting multiplex reactions in thousands of droplets and digital detection of different biomolecules in each of these droplets, thereby obtaining an absolute quantity of the target molecules in a sample for diagnostic or other analytical purposes. Since the measurement is real-time and down to a single molecule, the present invention provides more useful and accurate information than existing methods for end-point digital measurement.

In one embodiment, the present invention provides methods for implementing digital quantification and analysis of a bioassay, comprising four steps: 1) sample preparation, 2) sample compartmentalization, 3) reaction, and 4) digital detection.

In one embodiment, the present invention provides a diagnostic method for a disease, comprising a real-time and digital measurement of multiple biomolecules in a sample using the method or device described herein.

In one embodiment, the present invention provides a droplet microfluidic system, comprising: a droplet generator and a storage device containing a plurality of droplets, wherein each tiny hole of each storage device stores a droplet, wherein the droplet generator and the droplet storage device are integrated structure, wherein the droplet generator is in fluidic communication with the droplet storage device, each of pores being in fluidic communication.

In one embodiment, the droplet generator comprises an inlet and the droplet storage device comprises an outlet. In one embodiment, the droplet generator includes a plurality of inlets, each inlet is used for receiving a different reagent component, and one inlet is used for receiving a sample.

In one embodiment, the droplet generator is in fluidic communication with the droplet storage device via a microfluidic channel. In one embodiment, the material for making the microfluidic channel is selected from one or more of silicon, glass, plastic, and polydimethylsiloxane (PDMS). In one embodiment, the diameter of the microfluidic channel is 1-2 times the diameter of a droplet.

In one embodiment, the droplet generator is a droplet generating device based on surface tension. In one embodiment, the droplet generator comprises a cross-flowing structure that permits the continuous phase and dispersed phase to intersect at a particular angle θ. In one embodiment, the droplet generator comprises a step emulsion structure. In one embodiment, one inlet is used to receive a sample of cells or exosomes and the other one or more inlets are used to receive a lysis reagent or an oily substance when samples are cells or exosomes. In one embodiment, the height of a pore for storing droplets is 1-1.5 times the diameter of the droplets.

In one embodiment, the droplet storage chamber comprises rows of anchoring structure for anchoring the droplets to pre-determined positions in the droplet storage chamber. In one embodiment, the anchoring structure takes the form of pillars such as posts arranged in a way that is capable of trapping individual droplets. In one embodiment, the droplet contains no more than one copy or one target molecule to be analysed in subsequent steps.

DETAILED DESCRIPTION OF THE INVENTION

Definitions and Interpretations

Unless specifically stated otherwise, the words and terms of the present invention are to be explained by common meanings.

Detection

Detection is to analyze or test the presence of a substance or a material. The substance or material herein, for example, includes but not limited to a chemical substance, an organic compound, an inorganic compound, a metabolite, a drug or a drug metabolite, an organic tissue or a metabolite of an organic tissue, a nucleic acid, a protein or a polymer. In addition, the detection is also to test the amount of a substance or a material, and the assay includes immunoassay, chemical assay, enzyme assay and nucleic acid assay, etc.

The present invention provides methods and devices for detecting and quantifying multiple biomolecules at single-molecule level using an integrated droplet microfluidic system.

In one embodiment, the present methods and devices comprise an integrated droplet microfluidic system which is capable of generating thousands of droplets, thereby compartmentalizing a sample into thousands of isolated droplets for subsequent reactions and analysis per single droplet.

In one embodiment, the present invention enables real-time and digital measurement of multiple droplets generated from a sample by quantitative and independent measurement of a specific signal in each droplet.

In one embodiment, the present invention provides a diagnostic method for a disease, comprising real-time and digital measurement of multiple biomolecules in a sample using the method or device described herein.

As illustrated herein, the present invention introduces for the first time the concept of using a digital platform in microfluidic setting for co-detecting multiple biomolecules down to single-molecule level and quantifying these multiple biomolecules in a real-time manner, thereby allowing an efficient and accurate diagnosis.

By utilizing the present integrated droplet microfluidic system coupled with a motion and temperature control system and a detection unit, the present invention is capable of conducting multiplex reactions in thousands of droplets and digital detection of different biomolecules in each of these droplets, thereby obtaining an absolute quantity of the target molecules in a sample for diagnostic or other analytical purposes. Since the measurement is real-time and down to a single molecule, the present invention provides more useful and accurate information than existing methods for end-point digital measurement.

Figure 1:
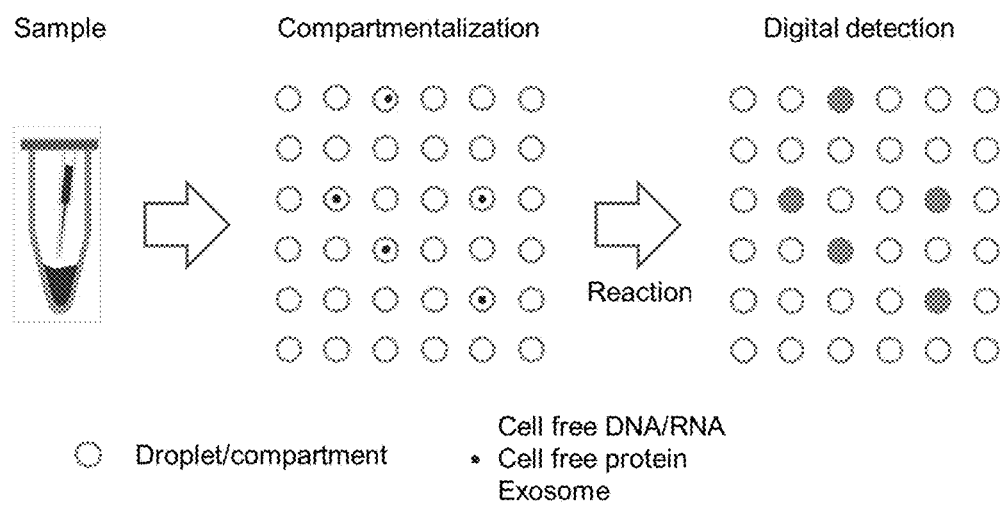
FIG. 1 shows one embodiment of the present invention for implementing a digital quantification bioassay, comprising four steps: 1) sample preparation, 2) sample compartmentalization, 3) reaction, and 4) digital detection.

In one embodiment, the present invention provides methods and devices for implementing digital quantification and analysis of a bioassay, comprising four steps: 1) sample preparation, 2) sample compartmentalization, 3) reaction, and 4) digital detection as illustrated in FIG. 1.

Figure 2:
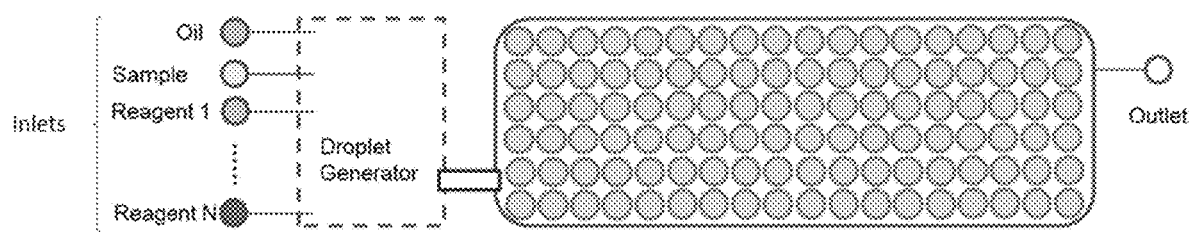
FIG. 2 shows one embodiment of the present invention comprising an integrated droplet microfluidic system for digital quantification bioassay.

FIG. 2 illustrates one embodiment of the present integrated droplet microfluidic system for digital quantification of bioassay, said system including four parts (from left to right): inlets, a droplet generator, a droplet storage chamber and an outlet. Inlets are used to introduce various liquids (e.g. oil, samples and reagents for carrying out reactions) to the droplet generator, wherein these liquids can be loaded separately through different inlets (as instantly shown in FIG. 2), or premixed and loaded as a mixture through the same inlet. Sample containing biomolecules is prepared and compartmentalized into isolated droplets through the droplet generator, the droplets generated are then spread in a one-layer configuration in a droplet storage chamber. After sample compartmentalization, parallel in situ reactions happen in individual droplets, where the reactions are part of a reaction assay for analyzing the target biomolecules, and the reactions in different droplets can be the same or different. Once the reactions are completed, signals indicating the presence of target biomolecules are detected by, for example, capturing the image of the droplets in the droplet storage chamber by a microscopic camera. The images are then processed by computer for digital counting and data analysis. Outlet is for removal of liquid or gas from the system. In one embodiment, outlet is for air or oil draining. In another embodiment where droplets need to be collected after reactions, they can be collected from the droplet storage chamber through the outlet.

Sample Preparation

The present invention can be applied to any type of samples containing target biomolecules. In one embodiment, the sample is a liquid sample obtained directly from a living organism including but not limited to human, animal, plant, fungi, microorganism such as bacterium and virus. In one embodiment, the sample is a solution containing the target biomolecules, wherein the solution can be obtained from another independent process that handles the target biomolecules. For example, the independent process is a process that isolates, purifies or concentrates the target biomolecules in a sample containing the target biomolecules, or a pre-treatment process that pre-treats a sample containing the target biomolecules with certain enzymes or reagents, under certain temperature or pressure.

Samples herein may include biological fluids. The initial state of samples or specimens may be liquid, solid or semi-solid. The solid or semi-solid samples may be converted to liquid samples by any suitable methods, such as mixing, mashing, maceration, incubation, dissolution, enzymatic hydrolysis, etc. Then the samples undergo digitalization processing i.e. droplet generation. During and before the digitalization processing i.e. droplet generation, samples may be treated, including filtration, dissolution, etc., or mixing with other reagents, to improve some performance of the samples and facilitate to provide better results in forming tiny droplets or detecting subsequently. Samples can be taken from humans, animals, plants, nature, etc. Samples taken from human body may be, for example, liquid samples, including blood, serum, urine, cerebrospinal fluid, sweat, lymph, saliva, gastric juice, etc.; solid or semi-solid samples including feces, hair, keratin, tartar, nails, etc. Samples taken from plants may be, for example, solid samples including roots, stems, leaves, etc., liquid or semi-solid samples including tissue fluid, cell fluid prepared from roots, stems, and leaves. Samples taken from nature may be, for example, liquid samples including rainwater, river water, seawater, and groundwater, etc., solid or semi-solid samples including soil, rock, ore, and petroleum, etc.

In one embodiment, samples include but are not limited to blood, plasma, serum, tissues, urine, saliva, fecal matters, smear preparations, and discharges such as tears, sputum, nasopharyngeal mucus, vaginal discharge and penile discharge. In one embodiment, samples include but are not limited to bacteria, viruses, bacteria cultures, viral cultures, cell cultures, cell suspensions, and adherent cells. In another embodiment, samples include but are not limited to food, feed, and plant.

In one embodiment, samples are taken directly from a subject. In one embodiment, samples are those which contain one or more biomolecules from a subject, including immediate or final products obtainable from various molecular assays such as polymerase chain reaction (PCR).

In one embodiment, the present invention comprises a step of providing or preparing a sample containing a target biomolecule to be detected or quantified by the present invention.

These target molecules or analytes are of different types. Different types of analytes are present in the same sample, for example, different biomolecules or different biomarkers. For example, in a cell, nucleic acids, proteins, polysaccharides, small molecule peptides are present. These different labeled substances or analytes are different. In the present invention, a base substabceis provided, for example, on a microfluid chip, to carry out detection of different types of analytes simultaneously, such as simultaneous detection of nucleic acids and proteins, simultaneous detection of nucleic acids and proteins associated with a disease, for example, nucleic acid mutations and protein molecule levels of a cancer or tumor. Here, the different types can also mean the same classification, but may have different meanings. For example, for detection of nucleic acids, DNA levels and RNA levels can be detected simultaneously. Here, the DNA levels and RNA levels can be considered different types of detection. For example, for protein levels, biologically labeled substances of different proteins can also be considered as different types of detection. For example, a plurality of protein molecules is associated with a disease, and these protein molecules have different polypeptide sequences, different protein three-dimensional structures, one or more of different sites, although they belong to the protein levels, the protein markers are different. The detection device or detection method of the present invention can also be used to simultaneously detect different types of protein molecules. For a specific disease, the contents of a variety of substances are provided and these substances are from the same sample, by this way, it reduce the number of times of sampling or reduce the amount of sample, and a variety of test results can be provided, for example, diagnosis of a disease.

In one embodiment, the size of a sample is 1 μL-500 μL. Too large of a sample volume may take a long time for droplet generation. Too small of a sample volume may lead to difficulty in loading the sample to the droplet generator.

In one embodiment, the viscosity of a sample is not larger than 0.5 Ns/m$^2$. In one embodiment, the sample does not contain solvent components which may cause droplets to merge such as DMSO.

Integrated Droplet Microfluidic System

In some specific embodiments, the present invention provides an integrated detection system or detection device, comprising a droplet generating device and a droplet storage device. The "integrated" herein means that the two components are connected into a single structure and form a whole structure, which can perform different functions at the same time, but these functions are carried out in a sequence and are integrated, to reduce the non-integrated operation steps. For example, in prior art, when a microfluidic system is used for detection, the liquid is generated by a separate droplet generation system, and when droplets are generated, another device is used to store the droplets, and usually a number of droplets are stored together. When reaction is necessary, the reaction is directly carried out in a storage container or it is transferred to a separate reaction device for reaction, such as incubation, heat cycling and amplification, etc. After the reaction is completed, the plurality of droplets are required to be separated for detection, for example, by a flow cytometer. The test results are read for droplets one by one. With many steps, the operation is cumbersome, which may also produce uncertainty to the final test results. For example, as there are many operation steps, different personnel may operate different batches, and increase the risk factors that affect the final test results; for example, frequent transfer of droplets will cause loss or fusion of droplets; for example, when mixing multiple droplets together for reaction, special attention should be paid to the control of incubation temperature because of the problem of uneven heat transfer; for example, multi-step transfer may cause cross-contamination and produce false positive results, affecting the accuracy of the experiment, which is particularly important in clinical tests. In the present invention, the functional components for forming droplets are combined with the reaction and detection, and only the samples are needed to prepare, and then all steps can be completed by one step, which greatly simplifies the operation steps, and reduces the adverse effect of different steps on the final detection.

Accordingly, in a specific embodiment, the present invention provides a detection system comprising a liquid generation system and a storage system. The storage system is used to store the droplets generated from liquid. In some embodiments, the droplet generating system is capable of generating a plurality of individual tiny droplets. The storage system includes a plurality of storage units, such as storage holes and cavities, each of which has a droplet stored therein. In some embodiments, the droplet generating system is in fluidic communication with the storage system via the microfluidic channel. The storage system herein includes a liquid inlet and an outlet, and there are a plurality of storage holes, chambers and cavities between the inlet and the outlet. It can be understood that the storage system herein can be directly used to perform a certain reaction. For example, the system in FIG. 2, includes a storage system (on the right side of FIG. 2), and the storage system includes a plurality of microporous structures, and each of which has a droplet stored therein. When these liquids include substances necessary for the reaction, for example, when performing nucleic acid amplification, there are primers and enzymes for amplification, etc., which can be directly given to the storage system for reaction. At this time, the storage system is a reaction container. The contain comprises a plurality of individual holes, and each hole has a separate droplet, and a separate reaction occurs in each droplet, and each droplet has a final result of independent reaction. When reaction ends, the reaction results can be detected for the storage system directly, and results of multiple independent reactions (multiple independent droplets) can be detected at one time. Compared to conventional multi-step testing, it is easy to operate for multiple different or identical test results.

Therefore, for generation of individual droplets, simultaneous detection of different types of analytes can be performed, for example, detection of nucleic acids and proteins, as described in detail later.

FIG. 2 illustrates one embodiment of the present integrated droplet microfluidic system for digital quantification of bioassay, comprising inlets, a droplet generator, a droplet storage chamber and an outlet In one embodiment, the present invention provides an integrated droplet microfluidic system for generating a plurality of isolated droplets from a sample.

In one embodiment, the present integrated droplet microfluidic system is configured as one single microfluidic chip.

In one embodiment, the present microfluidic system is formed by a droplet generator and a droplet storage chamber. In one embodiment, a sample containing biomolecules is compartmentalized into isolated droplets through a droplet generator, the droplets generated are then deposited in the droplet storage chamber in a one-layer configuration.

Inlets are used to introduce various liquids (e.g. oil, samples and reagents for carrying out reactions) into a droplet generator. As illustrated in FIG. 2, oil, sample and reagents 1 to N (i.e., various reagents required for subsequent reactions) are introduced into the droplet generator via different inlets. In one embodiment where the sample and reagents do not have chemical reactions, they can be premixed and loaded into the droplet generator as a mixture through one inlet. In another embodiment where the sample and one or more of the reagents react, these reagents and sample cannot be introduced into the droplet generator as a mixture but loaded into the droplet generator through different inlets and then compartmentalized into droplets at the junction of the droplet generator.

For example, where digital PCR for quantifying DNA through hot start amplification is to be carried out in a droplet, a sample containing the target nucleic acids and reagents for carrying out hot start amplification including primers, polymerases and other buffers can be premixed and loaded into the same inlet for droplet generation since reaction will only be started by raising the temperature to the working temperature of the polymerases. However, if enzymes in the reagents catalyse any substrate in the sample at room temperature, the enzyme-containing reagents and sample need to be loaded into the droplet generator through different inlets and then mixed within each droplet at the junction of the droplet generator.

Figure 3:
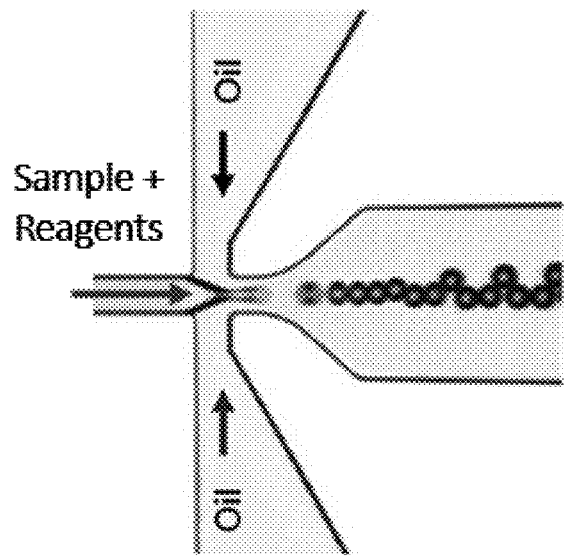
FIG. 3 shows one embodiment of droplet generation in the present invention.
Figure 4:
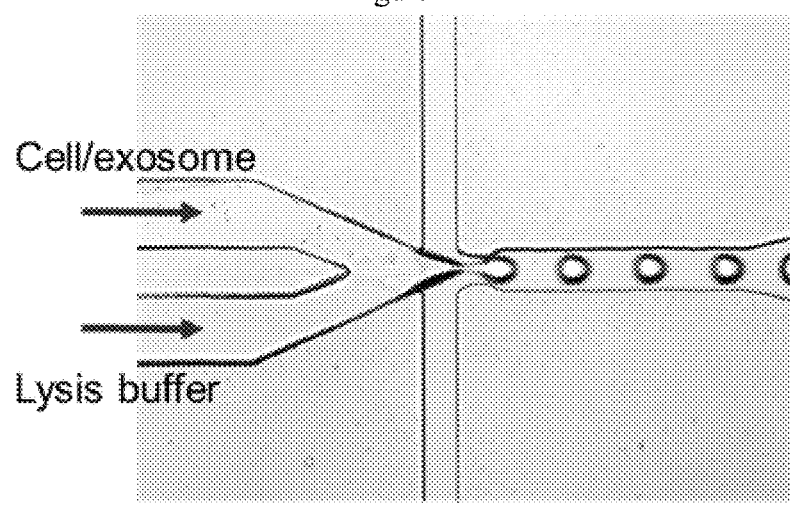
FIG. 4 shows another embodiment of droplet generation in the present invention.

FIG. 3 and FIG. 4 show two embodiments of droplet generation using the present invention. In FIG. 3, the original sample and reagents for carrying out subsequent reactions are premixed and the resulting mixture is subject to the droplet generator for encapsulation. In FIG. 4, since premixing of cells or exosomes and the lysis buffer will lead to lysis of the cells or exosomes, the original sample containing cells or exosomes and lysis buffer are loaded into the droplet generator via different inlets, such that they cannot be brought into contact before they are encapsulated into the droplets. In FIG. 4, since pre-mixing of cells or exosomes and the lysis buffer will lead to lysis of the cells or exosomes and inability to observe the expression at the single cell level, the original sample containing cells or exosomes and lysis buffer are loaded into the droplet generator via different inlets, such that they cannot be brought into contact before they are encapsulated into the droplets.

Droplet generators of the present invention can be of any structure or system that is capable of partitioning a liquid sample into a large quantity of droplets. In one embodiment, droplet generators include but are not limited to structures of flow focusing, T-junction and step emulsion.

Droplet storage chambers of the present invention can be any module that is capable of holding droplets generated by the droplet generators. In one embodiment, the design of the present droplet storage chamber depends on the total number and volume of droplets desired for specific assays.

In one embodiment, the droplets generated are spread in the droplet storage chamber in a one-layer configuration. After sample compartmentalization, parallel reactions are carried out in individual droplet in the droplet storage chamber, followed by detection and analysis of the target biomolecules.

In one embodiment, outlet is used to remove liquid or gas from the present integrated system. In one embodiment, outlet is for air or oil draining. In another embodiment where droplets need to be collected after reactions, they can be collected from the droplet storage chamber via the outlet.

In one embodiment, the present integrated droplet microfluidic system further comprises a unit for sorting and separation of droplets. For example, a sorting junction comprising electrodes in an alternating current (AC) electric field can be included in the present integrated droplet microfluidic system to select particular droplets which, for example, contain particular type of target molecules or have particular properties as indicated by fluorescent signals observed from the droplets (Baret, Jean-Christophe, 2009).

In one embodiment, the present integrated droplet microfluidic system comprises a plurality of microfluidic channels for delivering fluids to and from various components of the system. In one embodiment, the present droplet generator, droplet storage chamber and/or outlet comprises one or more microfluidic channels which set the flow paths of the fluids within these components. In one embodiment, one or more microfluidic channels are provided between different components of the integrated droplet microfluidic system (e.g. between droplet generator and droplet storage chamber) so as to direct fluid from one component to another component. In one embodiment, the exact type or configuration (e.g. structure, length, diameter, number of branches and density) of the microfluidic channels to be used depends on the purpose of having the microfluidic channels and the desirable flow resistance of individual components.

In one embodiment, microfluidic channels are made of materials selected from the group consisting of silicon, glass, plastics and polydimethylsiloxane (PDMS).

In one embodiment, the same type or configuration of microfluidic channels is used in various components of the present integrated droplet microfluidic system. In another embodiment, various types or configurations of microfluidic channels are used in various components of the present integrated droplet microfluidic system.

In one embodiment, the present droplet generator comprises two microfluidic channels for delivering oil and one or more microfluidic channels for delivering sample fluid and/or reagents. In one embodiment, the actual configuration depends on the type of emulsion chosen and the number of inlets required.

In one embodiment, a microfluidic channel is used to connect the droplet generator with the droplet storage chamber. In one embodiment, the microfluidic channel has a diameter 1-2 times the diameter of a droplet. Generally, a larger diameter of the microfluidic channel helps to stabilize the droplets as they pass through the channels, and constricting the fluid flow within the channel will also help to stabilize the droplets.

In one embodiment, the droplet storage chamber does not have any microfluidic channel and droplets generated will self-assemble to spread on the flat surface of the chamber. In cases where wells are present in the droplet storage chamber, droplets will be spread in the chamber and then guided into the wells by interfacial tension.

In one embodiment, the present outlet comprises a microfluidic channel which has a diameter of up to several hundred micrometers.

In one embodiment, the microfluidic channels are rectangular in shape (i.e., have a rectangular cross-section). In another embodiment, the microfluidic channels have a round cross-section.

Compartmentalization-Droplets Generation and Storage

In one embodiment, the present invention comprises a droplet generator which can be any structure or system that is capable of partitioning a liquid sample into a large number of droplets (e.g. thousands or millions of droplets). In one embodiment, droplet generators include but are not limited to structures of flow focusing, crossflowing, co-flowing, step emulsion and microchannel emulsification. P. Zhu and L. Wang (2017) describe a few technologies for droplet generations, the contents of which are hereby incorporated by reference in their entirely.

In one embodiment, the present droplet generator is a shear based droplet based droplet generating device which utilizes shear stress to pinch the fluid thread into small droplets. In one embodiment, shear based droplet based droplet generating devices include but are not limited to devices comprising a cross-flowing structure, a co-flowing structure and a flow focusing structure.

In one embodiment, the present droplet generator is an interfacial tension-based droplet generating device wherein interfacial tension is the dominant driving force in the process of droplet breakup. In one embodiment, interfacial tension-based droplet generating devices include but are not limited to devices comprising a structure of T-junction combining with step emulsion and a microchannel emulsification structure.

In one embodiment, the present droplet generator comprises a droplet generating structure described in WO2016189383A1, the contents of which are hereby incorporated by reference in their entirely into this application.

In one embodiment, methods that are capable of generating droplets can be utilized in the present invention for droplet generation, including but are not limited to high-shear stirring, ultrasonic emulsification, high-pressure homogenization and membrane emulsification.

In one embodiment, the present droplet generator comprises a flow focusing structure which constricts the flow to strength the focusing effect. In one embodiment, the flow focusing structure is a 2D planar flow focusing structure. FIG. 4 shows one embodiment of a droplet generating device comprising a flow focusing structure and a droplet storage chamber coupled downstream of the droplet generator. In FIG. 4, the sample at the center channel is sheared by fluid from side channels and breaks up into small droplets which are then sucked into the droplet storage chamber due to capillary force.

In one embodiment, the present droplet generator comprises a crossflowing structure which permits the continuous phase and dispersed phase to intersect at a certain angle θ. In one embodiment, the present droplet generator comprises a structure of T-junction, Y-junction, double T-junction, K-junction or V-junction.

In one embodiment, the present droplet generator comprises a co-flowing structure in which the dispersed fluid thread is punched off by the surrounding flow continuous phase. In one embodiment, the co-flowing structure is a 2D planar co-flowing structure.

In one embodiment, the present droplet generator comprises a step emulsion structure. In one embodiment, the present droplet generator comprises a step emulsion structure combined with a T-junction structure which is horizontal or vertical In one embodiment, the present droplet generator comprises a microchannel emulsification structure.

In one embodiment, the present droplet generator comprises a droplet generating structure described in WO2016189383A1, the contents of which are hereby incorporated by reference in their entirely into this application.

In one embodiment, components or parts of the droplet generator which is responsible for droplet generation (i.e. sample compartmentalization) have a hydrophobic surface. It can be accomplished by chemical surface coating by conjugating hydrophobic groups on the surface of the components or parts. In one embodiment, a surfactant such as Span 80, Tween 20 or Abil EM90 is added to the oil phase or water phase to avoid droplet coalescence or prevent molecules such as enzymes, DNA or RNA from adhering to the solid surface or water-oil interface.

In one embodiment, droplets are generated as emulsion droplets and are not limited to a particular type of emulsion. In one embodiment, emulsions include but are not limited to oil-in-water, water-in-oil and water-oil-water double emulsion.

In one embodiment, oil and surfactant are used for droplet generation. In one embodiment, the ratio of surfactant to oil is 1-5% (by weight). In one embodiment, oil to be used for droplet generations includes but is not limited to mineral oil, silicon oil, fluorinated oil, hexadecane and vegetable oil. In one embodiment, surfactant to be used includes but is not limited to Span 80, Tween 20/80, ABIL EM 90 and phospholipids. Surfactants that can be used in droplet-based microfluidics have been described by Baret, Jean-Christophe (2012), the content of which is hereby incorporated by reference in its entirety into this application.

Droplet storage chambers of the present invention can be any module that is capable of holding or preserving droplets, including but not limited to droplets that are generated by the droplet generators. In one embodiment, the design of the present droplet storage chamber depends on the total number and volume of droplets desired for reactions or assays to be performed in the subsequent steps.

In one embodiment, the size of the present droplet storage chamber is larger than the total volume of droplets generated. In one embodiment, the height of the present droplet storage chamber is 1-1.5 times the diameter of the droplets generated. As illustrated in FIG. 3, the height of the droplet storage chamber is 1-1.5 times the droplet diameter; the droplets are spread in the droplet storage chamber in a one-layer configuration.

In one embodiment, the present droplet storage chamber is coupled with the present droplet generator in a way that droplets generated are sucked into the droplet storage chamber by capillary force. In one embodiment, droplets are dispersed in the droplet storage chamber such that the droplets are packed in a specified manner. In one embodiment, droplets are dispersed in the droplet storage chamber such that the droplets are loosely or randomly packed.

Figure 5:
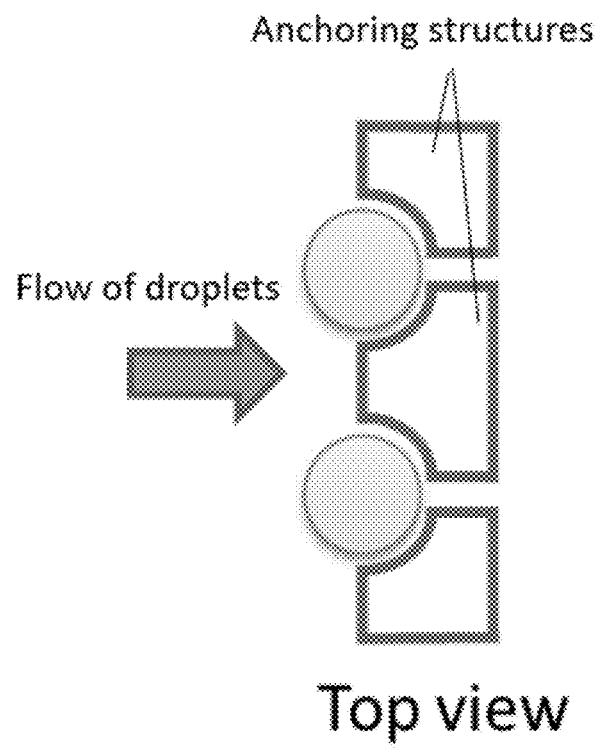
FIG. 5 shows one embodiment of anchoring structures in the droplet storage chamber. The anchoring structure strap individual droplets to pre-determined positions in the droplet storage chamber.
Figure 6:
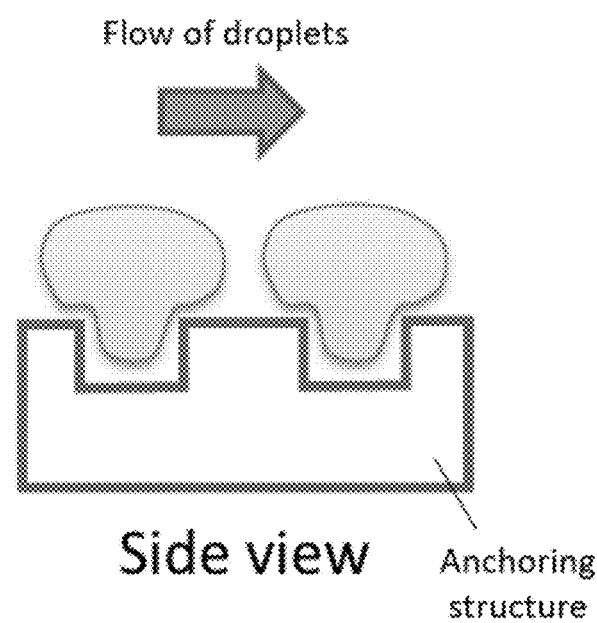
FIG. 6 shows another embodiment of an anchoring structure in the droplet storage chamber.
Figure 7:
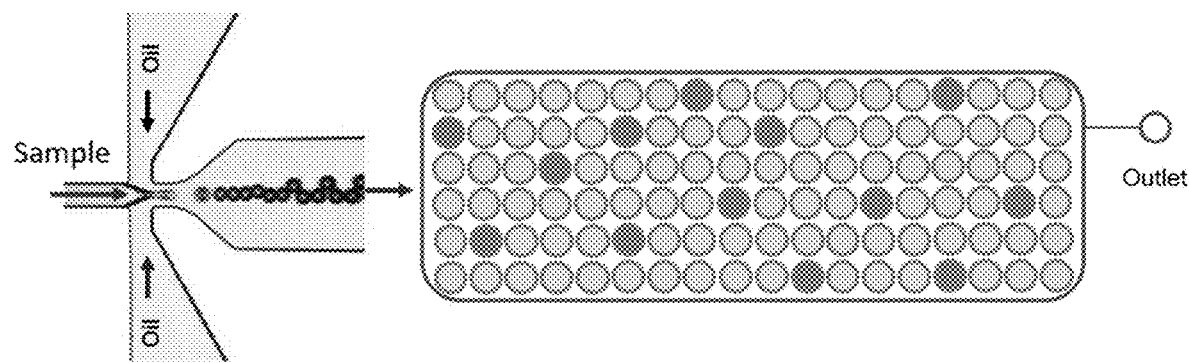
FIG. 7 shows one embodiment of a droplet generating device comprising a flow focusing structure coupled downstream with a droplet storage chamber.

In one embodiment where droplets are dispersed in a specific or pre-determined manner, the droplet storage chamber comprises rows of anchoring structure for anchoring the droplets to pre-determined positions in the droplet storage chamber. In one embodiment, the anchoring structure takes the form of pillars such as posts arranged in a way that is capable of trapping individual droplets (FIG. 5). As the droplets travel through the droplet storage chamber, they will be trapped in space between the pillars. In one embodiment, the anchoring structure takes the form of grooves which trap individual droplets by interfacial tension (FIG. 6). In one embodiment, the present droplet storage chamber comprises anchoring structures or equivalents described in the art, such as those described in Abbyad (2010) and Huebner (2008), the contents of which are hereby incorporated by reference in their entireties into this application.

In one embodiment wherein droplets are randomly packed, no anchoring structures are provided in the droplet chamber.

Droplet Characteristics

In one embodiment, the quantity, size (i.e., diameter), volume and type of emulsion of droplets generated or used by the present invention depend on the subsequent processing or analysis required.

In one embodiment, the number of droplets generated ranges from several hundreds to several millions.

In one embodiment, the size of the droplets generated ranges from about 5 μm to about 200 μm.

In one embodiment, the volume of the droplets generated ranges from about 0.65 fL (femtoliter) to about 4 nL (nanoliter).

In one embodiment, droplets generated are of uniform diameter. In one embodiment, droplets generated have a uniform diameter with coefficient of variation less than 5%. In another embodiment, droplets of varying diameters are generated by adjusting the loading pressure.

In general, droplets to be processed or analysed in one particular assay simultaneously in a droplet storage chamber (or an equivalent platform) are fairly uniform in size and volume to minimise influence on the results due to differences in droplet size or volume.

In one embodiment, each droplet produced by this invention contains no more than one copy of the target molecule (e.g. cell, exosome, or a certain type of biomolecule) to be analysed in subsequent steps. In one embodiment, the number of droplets to be produced and the volume of sample introduced for droplet generations are adjusted in a manner such that each produced droplet would contain no more than one target molecule. Digital methods which distribute target molecules into a large number of droplets theoretically follow the principle of Poisson distribution (Majumdar, 2015). Quantification of target molecules can then be done by counting the droplets which contain one or more copies of the target molecule. To achieve an absolute quantification, each droplet should contain no more than one copy of the target molecule. Generally, according to the principle of Poisson distribution, over 99% of droplets will contain no more than one copy of the target molecule if the ratio of the number of droplets to the number of target molecule is larger than 10, while the percentage will be 96% if the ratio is about 3. For example, when using the present invention for digital quantification of exosome, 10 times more antibody-conjugated beads than the expected number of exosomes is used to ensure that each bead will capture no more than one target exosome for an absolute quantification. Alternatively, in case a single copy of target molecule per droplet is not guaranteed (i.e., some of the droplets may contain more than one copy of the target molecule), Possion statistics are employed to calculate the absolute number of the target molecule (Majumdar, 2015).

The term "copy" as used in the present invention does not merely mean a copy of a nucleic acid in a usual sense, but refers to the number of target molecules, for example, one protein molecule in one sample can be a copy, and one nucleic acid molecule can be a copy of nucleic acid, a polypeptide chain molecule can be a copy of a polypeptide, so the copy herein may be a unit quantifier or a unit that can be quantified by number. Alternatively, a cell can also be called a copy of a cell, actually meaning a cell. When there are two cells, it can be called two copies of cells, although each cell is different, it only refers to two cells, only representing the quantity. Therefore, when a copy is used to measure a particular labeled substance or analyte (nucleic acid, DNA, RAN), it only indicates the number of labeled substances but not indicate whether the labeled substances or the target molecules are of the same type of substances. For example, 1 copy of DAN, RNA only indicates the number of DNA present, and when referring to 2 copies of DNA, it does not mean that two DNAs belong to the same DNA, which may be the same or different. For example, one of the samples is the DNA of A virus, and the other is the DNA of B virus. At this time, we can call 2 copies of DNA. For example, one droplet contains one copy of DNA of A virus, or contains two copies of virus DNA. At this time, two copies of virus DNA may be two DNA of A virus, or two DNA of B virus, or one DNA of A virus and one DNA of B virus.

In one embodiment, the present droplet generator is capable of achieving a high dynamic range by generating droplets of size and quantity that are sufficient for an accurate quantification of the target molecules in the sample. Generally, for digital analytical techniques which employ partitions (e.g. droplets) for detecting target molecules, the dynamic range of detection (i.e., the range of the number of target molecule that can be detected accurately using digital analytical technique) is determined by two main parameters: the size and total number of droplets, which are limited by the partitioning capability of the droplet generating device. For example, it was reported that the dynamic range of typical digital PCR is $0\text{-}10^6$, meaning that typical dPCR is unable to determine the absolute count of a target nucleic acid molecule in the sample if the level of that target nucleic acid molecule exceeds the limit of $10^6$ copies/μL. From statistics, having 3-10 times more droplets than target molecules will have a higher accuracy in detection but a smaller dynamic range. On the other hand, a larger dynamic range can be achieved by utilizing the Poisson distribution (Majumdar, 2015).

Multiplex Reactions in Multiple Droplets

As illustrated herein, the present invention provides a platform for carrying out multiplex reactions in all droplets and a real-time detection and quantification of target molecules in each of these droplets. Different from the end-point measurement in existing droplet-based technologies, this approach can provide a more efficient and accurate diagnosis.

In one embodiment, the present method comprises a step of carrying out multiplex reactions in the droplets generated by the integrated droplet microfluidic system.

In one embodiment, the present invention permits same type or different type of assays to be concurrently carried out in different droplets in a massive parallel manner.

In one embodiment, the same platform is used for droplet storage, for carrying out subsequent reactions or assays, and for detecting target molecules. For example, reactions can be carried out when droplets are dispersed in the present droplet storage chambers. In another embodiment, the platform for carrying out subsequent reactions or assays, and the platform for detecting target molecules are different. For example, when the method requires detection of DNA, the present invention uses a droplet generator for droplet generation, a PCR tube to store the droplets which are then subject to a PCR thermal cycler for reaction, and finally a droplet reader to detect the target molecule and produce a fluorescent signal readout.

Of course, the storage and reaction of droplets can be carried out in the same storage device. For example, if the storage device is in the form of a microfluidic chip, the amplification reaction is carried out in the same storage chip, and then the results of chip reaction are detected.

In one embodiment, after partitioning a sample into numerous isolated droplets and spreading the droplets in a droplet storage chamber, the present method and device carry out one reaction, of the same or different type, in every droplet in the droplet storage chamber concurrently. The present invention permits reaction in one droplet to be carried out independent of any other reactions in other droplets, therefore providing a high flexibility in conducting bioassay of any kind.

The term "reaction" as used herein refers to a reaction of a single droplet; specifically the substance necessary for the reaction in the droplets can indicate the presence or absence of one or more target molecules. For example, when there are multiple droplets, the reaction of each droplet is different, and the target molecule is also different. For example, one droplet performs nucleic acid test, the other droplet performs antibody antigen reaction, and other droplets have chemical color reaction. Of course, it is also considered that the DNA amplification reactions of class A specific DNA fragments exist in some individual droplets, and DNA amplification reactions of class B specific DNA fragments exist in some individual droplets, or different RNA reactions exist in different droplets. For example, messenger RNA amplification is performed in one droplet and transcription of RNA is performed in another droplet. By this way, individual reactions can be performed in individual droplets, to achieve the testing of different target molecules.

In one embodiment, reactions to be carried out after the compartmentalization are reactions that target the target biomolecules such that the target biomolecules can be detected or quantified in subsequent steps. In one embodiment, the reactions are any compatible bioassays used in the art. In one embodiment, reactions to be carried out are chosen depending on the nature of the target biomolecules.

In one embodiment, the biomolecule is a nucleic acid, a protein or a small molecule.

In one embodiment, the biomolecule is a cell-free molecule including but not limited to a cell-free DNA (cfDNA), a cell-free protein, an exosome and a cell-free molecule circulating in the body fluid of a subject. In one embodiment, the biomolecule is a molecule attached to the surface of a cell or inside a cell.

In one embodiment, the biomolecule is a nucleic acid of various types (e.g. DNA including cDNA, RNA including mRNA and rRNA), forms (e.g. single-stranded, double-stranded, coiled, as a plasmid, non-coding or coding) and lengths (e.g. an oligonucleotide, a gene, a chromosome and genomic DNA), originated from a subject or an exogenous source.

In one embodiment, the biomolecule is a protein which is a peptide or a polypeptide, including an intact protein molecule, a degraded protein molecule and digested fragments of a protein molecule. In one embodiment, biomolecules include but are not limited to antigens, receptors and antibodies, originated from a subject or an exogenous source.

In one embodiment, the biomolecule is a small molecule such as a metabolite. In one embodiment, the metabolite is a disease-related metabolite which is indicative of the presence or extent of a disease or a health condition. In one embodiment, the metabolite is a drug-related metabolite such as a drug by-product of which the level changes in a subject after consuming the drug.

In one embodiment, the target biomolecule is a molecule produced by a tumor or cancer, or by the body of a subject in response to a tumor or cancer.

In one embodiment, the target biomolecule is not normally found in healthy subject. In one embodiment, the target biomolecule is a molecule that is normally found in a healthy subject but the level of which is indicative of a particular disease or a health condition.

For example, biomolecules that are nucleic acids may require amplification by polymerase chain reaction (PCR) and labelling by complementary probes, while biomolecules that are proteins may require hybridization using antibody that recognizes certain epitopes of the proteins.

In one embodiment, where nucleic acids are to be detected and quantified, reactions include but are not limited to polymerase chain reaction (PCR), reverse transcription-PCR (RT-PCR), real-time PCR, and real-time RT-PCR, reverse transcription, labeling, digestion, blotting procedures, enzyme-linked immunosorbent assay (ELISA), radioimmunoassay (RIA), immunoassays and enzymatic assays. For example, ddPCR™ EGFR Exon 19 Deletions Screening Kit (Bio-Rad Laboratories, Inc.) is used to screen for mutations of 15 deletions in Exon 19 of the EGFR gene. Other deletions in this region of the EGFR Exon 19 may also be detected by this kit. EGFR Exon 19 deletions are commonly associated with melanoma, colorectal, and lung cancers.

In one embodiment, where biomolecules of protein nature (e.g. protein, peptide, antibody) are to be detected and quantified, reactions include but are not limited to ELISA-based reactions, labeling of target protein by target-specific signaling moiety and reactions that are catalyzed or inhibited by the target protein. For example, Alpha-Synuclein Discovery Kit (Quanterix™) can be used to detect the presence of Alpha-Synuclein (α-Synuclein) which has a propensity to form toxic soluble oligomers (i.e., protofibrils) that ultimately aggregate into insoluble fibrils. α-Synuclein was reported to be linked to the pathogenesis of Parkinson's disease, dementia of Parkinson's disease, dementia with Lewy bodies, and possibly Alzheimer's disease.

In one embodiment, where exosomes are to be detected and quantified, reactions include but are not limited to reactions for labeling, detecting or quantifying exosome-specific biomolecules. For example, by quantifying exosomes with target Glypican (GPC-1), an exosomal membrane protein which has much higher expression on cancerous exosomes than noncancerous exosomes, from a variety of exosome subpopulation protein biomarkers, is able to differentiate serum samples from breast cancer patients and healthy persons (Liu, 2018). In one embodiment, absolute count of exosomes carrying one or more specific biomolecules can be determined digitally using ExoELISA method. In one embodiment, the method used is the method described in Liu (2018), the content of which is hereby incorporated by reference in its entirety into this application.

In one embodiment, instead of detecting and quantifying the exosomes in a sample, target molecules (and optionally with non-target molecules) are extracted from the exosomes and subsequently detected and quantified by the present invention (Chen, 2013; Li 2018). Yet in another embodiment, both the exosomes and target molecules are detected and quantified using the present methods including but not limited to that described in Example 2. One skilled in the art will be able to choose the appropriate analytical approach for a particular disease or purpose in view of the present disclosure and knowledge in the art.

In one embodiment, when pathogens are to be detected and quantified, reactions include but are not limited to reactions for labeling, detecting or quantifying pathogen-specific biomolecules such as DNA, RNA or viral/bacterial antigen. For example, human immunodeficiency virus (HIV) can be detected and quantified by quantifying its DNA using appropriate kits and droplet digital PCR. It is believed that DNA of HIV provides the most sensitive measurement of residual infection in patients on combination antiretroviral therapy (cART) (Strain, 2013).

In one embodiment, reactions are carried out in each of the droplets generated.

In one embodiment, reactions to be carried out in each of the droplets are of the same type. In another embodiment, reactions to be carried out in each of the droplets are of different types. In yet another embodiment, reactions to be carried out in some of the droplets are of the same type, while reactions to be carried out other droplets are of different types.

In one embodiment, operating conditions (e.g. temperature, pressure and duration) for carrying out the reactions in each of the droplets are the same. In one embodiment, one or more operating conditions for carrying out the reactions in each of the droplets are different.

In one embodiment, target-specific compositions are included in the reactions so as to recognize and label target biomolecules in the droplets. In one embodiment, target-specific compositions are molecules that can specifically recognize a target biomolecule by means of structural recognition, functional recognition, or both.

In one embodiment, target-specific compositions are used to identify and label a specific type or species of biomolecule in the droplets. In one embodiment, target-specific compositions are primers or probes comprising nucleic acids that contain sequence complementary to the target nucleic acids. In one embodiment, target-specific compositions are probes, antibodies or equivalents that recognize specific epitopes or spatial configurations possessed by a target biomolecule such as a protein, peptide and viral particle.

In one embodiment, target-specific compositions are molecules that can be processed (e.g. digested, reduced, oxidized, or otherwise modified) by the target biomolecules. For example, where an enzyme is the target biomolecule, target-specific compositions can be a small-molecule substrate that is subject to the enzymatic reaction catalyzed by that enzyme.

In one embodiment, target-specific compositions comprise one or more signal-generating moieties that generate detectable signals so that the target biomolecules can be detected and quantified in subsequent steps of detection and analysis.

In one embodiment, signal-generating moieties include but are not limited to chemiluminescent, fluorescent, and chromogenic substrates, as well as other substrates that are convertible to a product capable of being detected.

Digital Detection and Quantification of Target Biomolecules

In one embodiment, the present invention comprises detection of target molecules using systems or devices that are capable of detecting signals indicative of the target molecules.

In one embodiment, the present method comprises a step of measuring the absolute count of signals indicating the presence of target biomolecules and thereby quantifying the target biomolecules in an absolute count. In one embodiment, the present method measures signals generated by the signal-generating moieties described herein.

In one embodiment, the present method comprises a step of quantitatively and independently measuring a specific signal from a plurality of droplets. Digital means the signal is either one or zero. For instance, the droplets with fluorescence are named as 'positive' (i.e., the droplets contain target molecule) and the droplets without fluorescence are 'negative' (i.e., no target molecule is present in the droplets).

Figure 8:
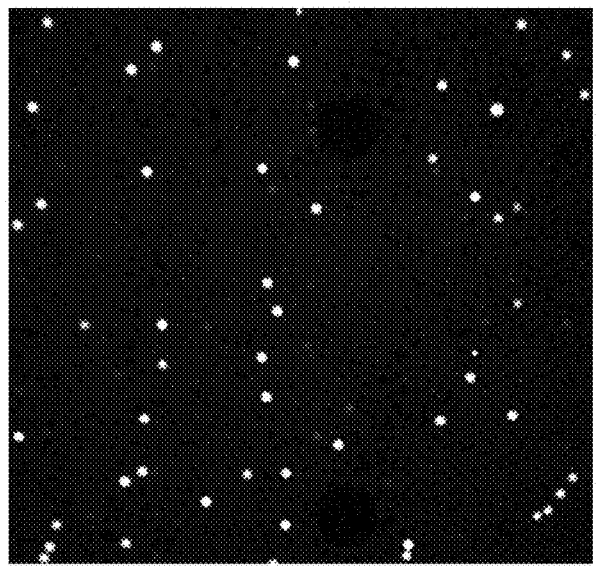
FIG. 8 shows a florescence image of droplets obtained by a CCD camera.

In one embodiment, signals to be detected are fluorescent signals, and systems or devices that are capable of capturing fluorescent signals and measuring the intensity of fluorescent signals are used. In one embodiment, a charge-couple device (CCD) is used to capture fluorescent signals and generates images of florescent droplets deposited in a chamber or on a chip. By counting the number of fluorescent droplets and intensity of fluorescent signals in each of the droplets, the florescent signals can be processed and analyzed. In one embodiment, florescent signals measured are processed and analyzed using a proprietary image processing code. FIG. 8 shows a florescence image of droplets obtained by a CCD camera.

In one embodiment, only one type of biomolecule is detected and quantified per single droplet.

In one embodiment, two or more types of biomolecules are detected and quantified per single droplet. For example, protein, nucleic acids, exosomes and/or other type of biomolecules are detected and quantified one after another in one single droplet.

In one embodiment, two or more species of biomolecules of the same type are detected and quantified per single droplet. For example, two or more species of nucleic acids (e.g. a DNA molecule and a RNA molecule) are detected and quantified per single droplet.

In one embodiment, when two or more types of biomolecules are to be detected and quantified per single droplet, one type of biomolecules is first detected and quantified per single droplet, then another type of biomolecules is detected and quantified per single droplet, and so forth. For example, one or more species of nucleic acids are first detected and quantified per single droplet, and then one or more species of peptides are detected and quantified per single droplet thereafter.

In one embodiment, the type of biomolecules detected and quantified in one droplet is different from the type of biomolecules detected and quantified in another droplet.

In one embodiment, the present invention detects 1-5 types of biomolecules per run. In another embodiment, the present invention detects 6-10 types of biomolecules per run. In yet another embodiment, the present invention detects 11-20 types of biomolecules per run.

In one embodiment, the present invention detects 1, 2, 3, 4, 5, 6, 7, 8, 9 or 10 types of biomolecules per run.

Downstream Applications

In one embodiment, droplets produced are optionally collected for subsequent storage or downstream analysis. In one embodiment, droplets are collected from the outlet of the present integrated droplet microfluidic system. The collected droplets can be disrupted to extract and recover biological materials within the droplets. For instance, amplified DNA products in preceding reactions can be recovered from the droplets and subjected to further processing such as new-generation sequencing.

In one embodiment, all droplets generated are collected from the outlet, disrupted to obtain a suspension of their content. The suspension is then partitioned into droplets and analyzed using the method or device described herein.

In one embodiment, all droplets generated are collected from the outlet and then sorted for containing a target molecule. For example, the collected droplets can be loaded into a microfluidic sorting device for screening. In brief, droplets collected are injected into the sorting device as a monodisperse emulsion, and the emulsion droplets are kept apart with surfactant-free fluorinated oil. The droplets are deflected as they pass through a sorting junction having an alternating current (AC) electric field (Baret, Jean-Christophe, 2009).

In one embodiment, droplets collected from the outlet or sorted are subject to further manipulation such as treatment with addition of reagents and incubation under appropriate conditions.

Examples 2-5 describe detection of different types of biomolecules using the present invention. The following are explementary descriptions illustrating how the present invention can be used to detect or quantify a wide range of biomolecules that are indicative of a disease state. However, one skilled in the art will readily appreciate that the examples and descriptions provided are merely for illustrative purposes and are not meant to limit the scope of the invention which is defined by the claims following thereafter.

Detection of Microorganism by Co-Detection and Quantitation of DNA and RNA

In one embodiment, the present invention provides a method for detecting a pathogenic microorganism present in a sample such as food, feed and plant, or any solution or suspension derived therefrom. The present method is important in ensuring the safety of food as well as preventing the spread of microbes.

In one embodiment, the method for detecting a pathogenic microorganism comprises a step of detecting and quantifying biomolecules that are indicative of the presence of the pathogenic microorganism in question, wherein the method partitions the sample into droplets and performs digital detection and analysis against the target pathogenic microorganism using methods and devices described herein. In one embodiment, biomolecules to be detected are nucleic acids and/or proteins possessed by the target pathogenic microorganism.

In one embodiment, multiple species of nucleic acids of the target pathogenic microorganism are detected and quantified by the present invention. Since the genome of a pathogen can be made of DNA, RNA or both, a multi-functional detection or diagnostic tool that is able to amplify and detect both RNA and DNA targets in an efficient and sensitive manner would be particularly useful in clinical practices. Example 2 provides one example of co-detecting DNA and RNA down to the single molecular level. By detecting or quantifying related DNA or RNA biomarkers, the present invention can be used for detecting any organisms, tissues, cells and moieties, alive or dead, comprising these DNA or RNA biomarkers.

In one embodiment, nucleic acids and protein of the pathogenic microorganism are detected and quantified concurrently by the present invention.

Co-Detection and Quantitation of Nucleic Acids and Proteins

In one embodiment, the present invention provides a method for co-detecting nucleic acids and proteins in a sample.

In one embodiment, the present invention provides a method for co-detecting and/or quantifying one or more protein markers and one or more nucleic acid markers indicative of a certain disease or health condition, thereby determining the existence or extent of such disease or health condition in a subject.

Example 3 provides one example of co-detecting and quantifying multiple protein markers and nucleic acid markers for detecting solid tumors prior to metastases.

For example, it was reported that a combination of four protein biomarkers with one genetic marker (KRASmutation) could enhance the sensitivity for the detection of pancreatic cancers (Cohen, 2017), and a blood test can detect eight common cancer types (ovary, liver, stomach, pancreas, esophagus, colorectum, lung, and breast) through assessment of the levels of circulating proteins (8 proteins) and mutations in cell-free DNA (16 genes) (Cohen, 2018).

Co-Detection and Quantitation of Proteins and Messenger RNA (mRNA)

In one embodiment, the present invention provides a method for co-detecting proteins and mRNA in a sample. Example 4 provides one example of co-detecting and quantifying proteins and messenger RNA in a sample.

Integrated co-detection of proteins and mRNAs from the same cell has the potential to not only reveal the correlation between these two classes of biologically important molecules, but also help understand the mechanisms of gene regulation, at both the transcriptional and translational levels.

Co-Detection and Quantitation of DNA, RNA and Protein in an Exosome

In one embodiment, the present invention provides a method for co-detecting and quantifying DNA, RNA and protein in an exosome. In another embodiment, the present invention provides a method for quantifying the number of exosomes in a sample in an absolute manner.

Example 5 provides one example of co-detecting and quantifying DNA, RNA and proteins in a single exosome, and absolute quantification of exosomes in a sample.

Exosome contains biomolecules including DNA, RNA and protein within its lumen or on its lipid membrane. These molecules can be extracted from an exosome isolated from a sample such as serum. With the present invention, absolute count of exosomes can be achieved digitally using ExoELISA method, or absolute count of individual biomolecules such as DNA, RNA or protein can be achieved digitally using digital PCR or digital ELISA. Information about the count of these biomolecules can be coupled or pooled for analysis for diagnostic purpose or otherwise.

Evaluation of the Validity of Results of a Bioassay

In one embodiment, the present invention provides a method for evaluating the validity of results of a bioassay based on the quantity of target biomolecules determined by the steps described above. For example, where the quantity of a target biomolecule in a sample is found to fall below the detection limit of a bioassay, or the relative amount of DNA and RNA molecules in a sample is found to fall outside the normal ranges, the results obtained by the bioassay may not be accurate. A newly collected sample or concentration of the original sample may be needed to validate the results.

Determination or Evaluation of the Health Status of a Subject

In one embodiment, the present invention provides a method for determining or evaluating the health status of a subject based on the quantity of target biomolecules determined by the methods or devices described herein.

Since the present invention provides an accurate quantification of target molecules in a highly specific and sensitive manner, the present invention can significantly improve the sensitivity, specificity and accuracy of biomarker-based diagnostic tests, in particular those which rely on the absolute quantity of the biomarkers. For example, by providing an accurate absolute count of a pathogen or a type of cancer cell in a subject, the present invention can differentiate patients of various risk levels, infectious levels, or having different stages of cancer.

In one embodiment, the present method comprises a step of determining the presence or absence of a condition that is indicative of a disease or health condition of a subject based on the quantity of target biomolecules determined by the methods or devices described herein.

In one embodiment, the present method comprises a step of determining the stage of progression of a disease based on the quantity of target biomolecules determined by the methods or devices described herein.

In one embodiment, the present method comprises a step of evaluating a drug response of a subject based on the quantity of target biomolecules determined by the methods or devices described herein.

In one embodiment, diseases to be detected or diagnosed using the present methods or devices include, without limitation, cancers, infectious diseases, endocrine diseases, metabolic diseases, genetic diseases, diseases of the nervous system and sense organs, diseases of the circulatory system, diseases of the respiratory system, diseases of the digestive system, diseases of the genitourinary system, diseases of the skin and subcutaneous tissue, diseases of the musculoskeletal system and connective tissue, and congenital anomalies.

In one embodiment, the present invention provides a method for real-time and digital count of target biomolecules in a sample containing said target biomolecules, the method comprises the steps of:
  a) providing to a droplet generator said sample and reagents suitable for said method;
  b) generating droplets with said droplet generator, wherein some droplets contain said reagents and said target biomolecules;
  c) allowing said reagents to label said target biomolecules, producing fluorescent signals;
  d) detecting fluorescent signals from all droplets; and
  e) converting said signals into digital values to obtain the total number of said target biomolecules in said sample.

In one embodiment, the present invention provides a method for real-time and digital count of cells or exosomes containing target biomolecules in a sample containing said cells or exosomes, the method comprises the steps of:
  a) providing to a droplet generator said sample and reagents suitable for said method;
  b) generating droplets with said droplet generator, wherein some droplets contain said reagents and said cells or exosomes;
  c) allowing some of said reagents to lyse said cells or exosomes to release said target biomolecules, and then some of said reagents to label said target biomolecules, producing fluorescent signals;
  d) detecting fluorescent signals from all droplets; and
  e) converting said signals into digital values to obtain the total number of said cells or exosomes in said sample.

In one embodiment of the present method, wherein in step b) each of said some droplets contains no more than one copy of the target biomolecules of the same type. In one embodiment, wherein in step b) each of said some droplets contains no more than one copy of the cells or exosomes.

In one embodiment of the present method, wherein the target biomolecules to be labelled in step c) are of the same type or different types.

In one embodiment of the present method, wherein the method detects 1-10 types of target biomolecules.

In one embodiment of the present method, wherein the target biomolecules are selected from the group consisting of nucleic acids, peptides, proteins, enzymes, viruses and microorganisms.

In one embodiment of the present method, wherein the nucleic acids are selected from the group consisting of coding DNA, non-coding DNA, messenger RNA, ribosomal RNA, micro-RNA and transfer RNA.

In one embodiment of the present method, wherein steps (c) and (d) are performed concurrently to detect fluorescent signals in real time.

In one embodiment of the present method, wherein step (d) is performed continuously or intermittently when the target biomolecules are being labelled in step (c).

In one embodiment of the present method, wherein the method further comprises a step of collecting the droplets after any one of steps (c)-(e).

In one embodiment of the present method, wherein the droplets collected are disrupted to obtain a suspension comprising labelled target biomolecules.

In one embodiment of the present method, wherein the droplets collected are introduced to a droplet sorting unit to select droplets containing a particular type of target biomolecules or having particular properties.

In one embodiment of the present method, wherein the droplet generator comprises a structure selected from the group consisting of a flow focusing structure, a crossflowing structure, a co-flowing structure, a step emulsion structure and a microchannel emulsification structure.

In one embodiment of the present method, wherein the sample and reagents are introduced to the droplet generator through the same inlet or different inlets.

In one embodiment of the present method, wherein fluorescent signals are detected by a charge-couple device.

In one embodiment of the present method, wherein the droplets have a diameter in the range of 5 μm to 200 μm.

In one embodiment of the present method, wherein the quantity of droplets generated ranges from several hundreds to several millions.

In one embodiment of the present method, wherein the method is carried out on an integrated droplet microfluidic system comprising said droplet generator, a droplet storage chamber, a detection unit and a plurality of microfluidic channels.

In one embodiment of the present method, wherein the total number of said target biomolecules is indicative of the severity or lack of a disease.

In one embodiment, the present invention provides a method for diagnosing a disease in a subject, the method comprises the step of determining the absolute quantity of a biomarker of said disease in a sample of the subject, wherein said absolute quantity is determined by using any one of the methods described above, wherein said biomarker is the target biomolecule present in said sample or present in the cells or exosomes in said sample, wherein the absolute quantity of said marker as compared to a control indicates the presence, severity or absence of said disease in said subject.

Throughout this application, various publications are cited. The disclosures of these publications in their entireties are hereby incorporated by reference into this application to more fully describe the state of the art to which this invention pertains.

Throughout this application, it is to be noted that the transitional term "comprising", which is synonymous with "including", "containing" or "characterized by", is inclusive or open-ended, and does not exclude additional, un-recited elements or method steps.

This invention will be better understood by reference to the examples which follow. However, one skilled in the art will readily appreciate that the examples provided are merely for illustrative purposes and are not meant to limit the scope of the invention which is defined by the claims following thereafter.

EXAMPLES

Example 1-Integrated Droplet Microfluidic System

This example illustrates one embodiment of the present digital quantification system which is integrated in one microfluidic chip. The microfluidic chip is formed by a droplet generator and a droplet storage chamber. The droplet generator can be the structures of flow focusing, T-junction or step emulsion. The droplet storage chamber design depends on the total number and volume of droplets desired for a specific assay. The height of the chamber is usually 1~1.5 times the diameter of the droplets and the size of the chamber is larger than the total volume of the droplets. The resulting droplets are spread in a one-layer configuration on a microfluidic chip. After the sample compartmentalization is finished, reactions happen in situ in parallel in all droplets. Once the reactions are completed, a microscopic camera and a X-Y motion stage are coupled together to take the image of the droplets on the whole microfluidic chip. The images are processed by a computer for digital counting and data analysis.

FIG. 1 shows one embodiment of the present integrated droplet microfluidic system.

FIG. 2 shows one embodiment of the present invention comprising an integrated droplet microfluidic system for digital quantification of biomolecules inside each of the droplets. The present microfluidic system includes four parts (from left to right): inlets, a droplet generator, a droplet storage chamber and an outlet. Inlets are used to introduce various liquids (e.g. oil, samples and reagents for carrying out reactions) to the droplet generator, where these liquids can be loaded separately through different inlets (as shown in FIG. 2), or premixed and loaded as a mixture through the same inlet. Sample containing biomolecules is prepared and compartmentalized into isolated droplets through the droplet generator; the droplets generated are then spread in a one-layer configuration in a droplet storage chamber. After sample compartmentalization, parallel in situ reactions happen in the individual droplets, wherein the reactions are part of a reaction assay for analysing the target biomolecules, and the reactions in different droplets can be the same or different. Once the reactions are completed, signals that indicate the presence of target biomolecules are detected by, for example, capturing the image of the droplets in the droplet storage chamber using a microscopic camera. The images are then processed by computer for digital counting and data analysis. Outlet is for removal of liquid or gas from the system. In one embodiment, outlet is for air or oil draining. In another embodiment when droplets need to be collected after reactions, they can be collected from the droplet storage chamber through the outlet.

Example 2-Co-Detection and Quantitation of DNA and RNA from a Single Cell/Exosome at the Molecular Level This example illustrates one example of using the present invention for the detection of pathogenic microorganisms present in food, feed, plant, or other samples. This is important for providing safe food as well as for preventing the spread of microbes. Since the genome of pathogens is made of DNA and/or RNA, a multi-functional diagnostic tool that is able to amplify and detect both RNA and DNA targets in an efficient and sensitive manner would be particularly useful in clinical practices.

For DNA targets, digital PCR can be used for absolute counting of DNA molecule using specific primers and reagents co-encapsulated in the droplets.

For RNA targets, digital RNA counting can be accomplished by digital PCR after the reverse transcription of the RNA extracted from cells. However, such method for absolute counting of RNA provides only the averages of cell ensembles and thereby unveils only the average genotypic/phenotypic traits of the cell population. For absolute counting of the RNA from a single cell or exosome, a system such as shown in FIG. 9 can be used, involving two rounds of encapsulation: one for single cell or exosome, and the other for single mRNA molecules.

Figure 9:
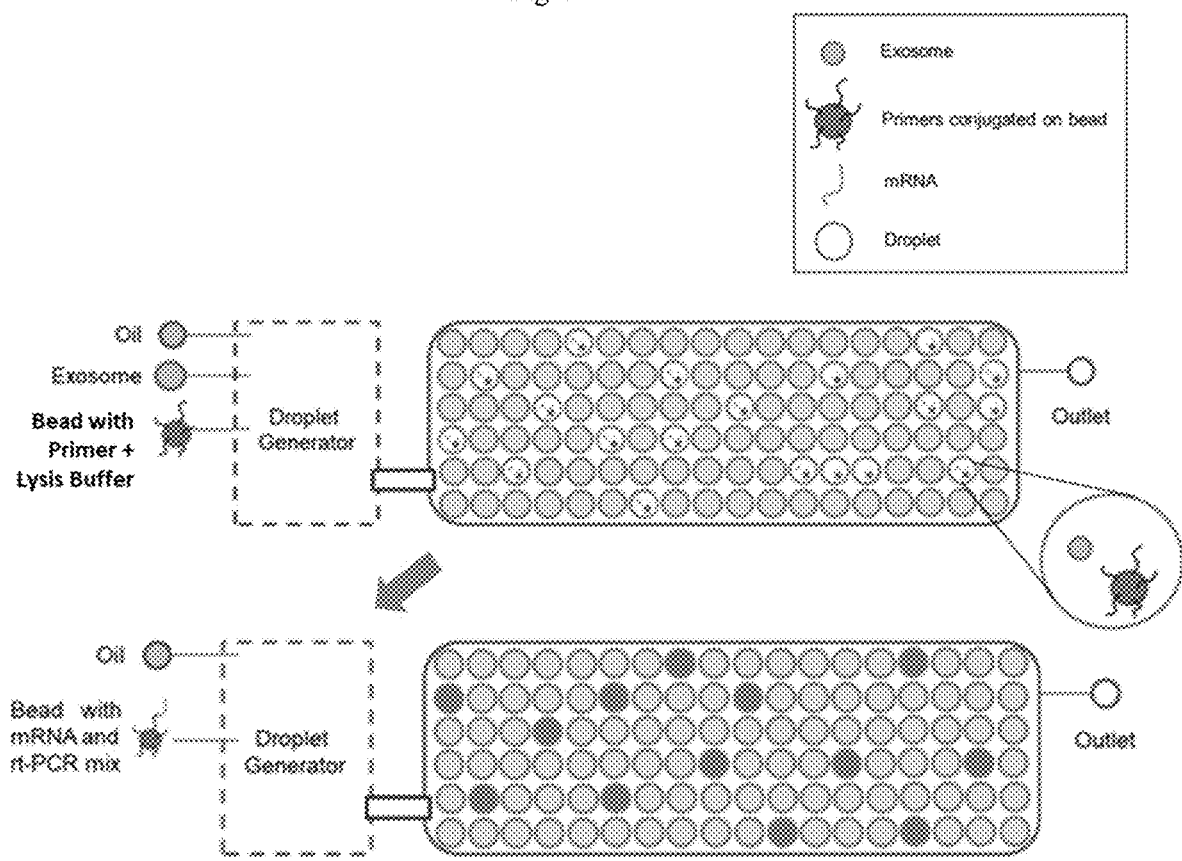
FIG. 9 shows one embodiment of the present integrated droplet microfluidic system for digital quantification of RNA from a single exosome.

As shown in the upper panel of FIG. 9, a single exosome (or single cell as the case may be), magnetic beads conjugated with primer specific to the target RNA and lysis buffer for lysing the exosome or cell are encapsulated into one droplet by the droplet generator. Droplet generation may take the form shown in FIG. 4. After droplets are generated, they are stored in the droplet storage chamber at the right. In each isolated droplet, the single exosome is lysed and the RNA contained therein is released and paired with the target-specific primer on the magnetic beads. Droplets are then collected from the outlet for subsequent analysis. All the collected droplets are then broken using a solvent (e.g. Perfluoro-1-octanol) to dissolve the oil phase and obtain an aqueous suspension of the magnetic beads with RNA from the single cell/exosome. A washing solution (e.g. PBS) is then added to the suspension followed by mixing with vortex. The mixture is then allowed to settle on a magnetic shelf. Components that are not necessary for subsequent rt-PCR reactions would be removed together with the washing solution by pipetting while the magnetic beads with primer conjugated with the target RNA are retained.

Figure 10:
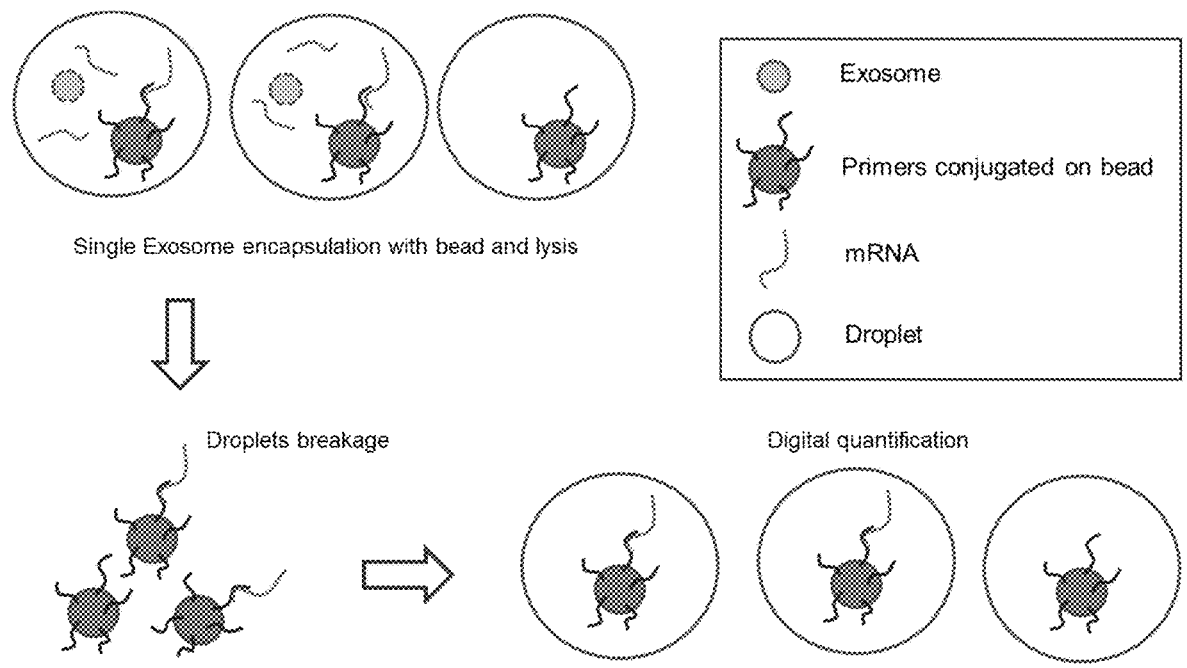
FIG. 10 shows a process of digital quantification of RNA from a single exosome.

As shown in FIG. 10, mRNA molecules from one exosome are released after lysis of the exosome and will be conjugated with a target primer on the magnetic beads. Unnecessary components are washed away through washing steps. The resulting sample containing the beads with primer conjugated with mRNA will then be encapsulated into droplets for digital quantification of the mRNA.

As shown in the lower panel of FIG. 9, the magnetic beads with primer conjugated with mRNA are mixed with a reverse transcription mixture and PCR mixture (collectively rt-PCT mix) and then loaded into an integrated droplet microfluidic system for in situ reverse transcription and PCR thermal cycling. Droplet generation may take the form shown in FIG. 3 since reverse transcription and PCR are hot start reactions and therefore the mRNA sample and rt-PCT reaction mix can be pre-mixed before encapsulation. Fluorescent signals (as indicated by the darker dots in the droplet storage chamber in the lower penal of FIG. 9) are then detected digitally through a microscopic camera and absolute count of the RNA target from a single cell or exosome can be calculated.

Figure 11:
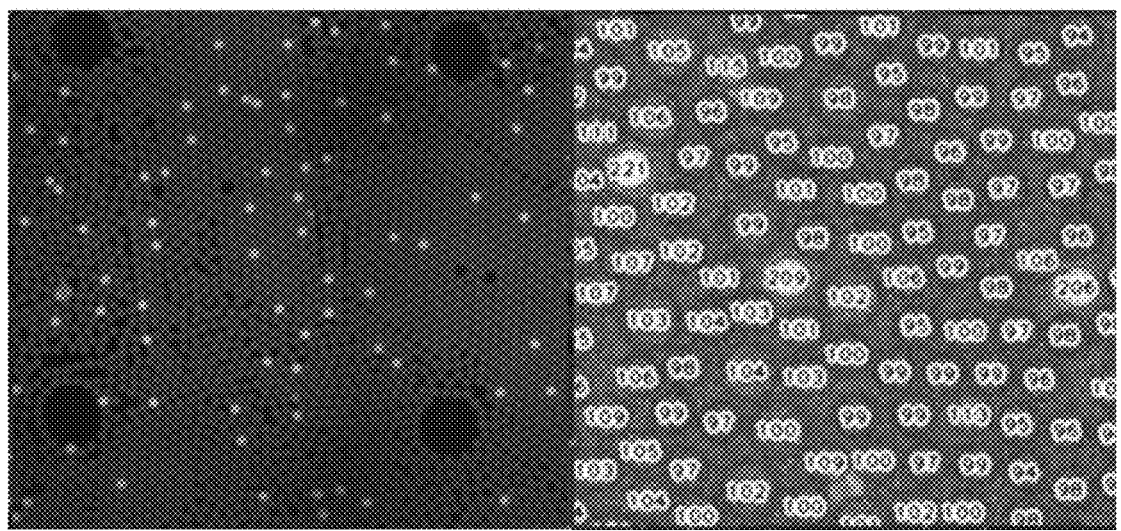
FIG. 11 shows two images of the fluorescent signals obtained from droplets containing amplified DNA molecules in an end-point digital detection of target DNA molecules using the present invention.

FIG. 11 shows data of end-point digital detection of DNA using the present invention. PCR thermocycling was performed to amplify the target DNA in a sample. The resulting mixture was then partitioned into 100,000 droplets which were subsequently spread in the present droplet storage chamber in a one-layer configuration. Florescent signals that were indicative of the presence of target DNA were recorded using a camera and the intensity of fluorescent signals in each droplet was measured using an image processing program. The image on the left records fluorescent signals detected from droplets located in one region of the droplet storage chamber, while the image on the right shows the intensities of fluorescent signals of each of the droplets located in another region of the droplet storage chamber (each circle represents one droplet and a higher numerical value indicates a higher level of fluorescent signal). Absolute count of the target DNA was then calculated based on the signals detected.

In cases where multiple RNA molecules are to be detected from a population of cells or exosomes, it is possible that some cells or exosomes may not contain every species of the target RNA molecules, or some cells or exosomes may contain fewer or more species of target RNA molecules than the other cells or exosomes. Through the two-round encapsulation process described herein, the present method is capable of extracting single molecules from a population of cells or exosomes and analyzing target RNA molecules from each of these cells or exosomes. Both the number of cells or exosomes in the population, the number of cells or exosomes containing the target RNA, and the number of target RNA molecules from each cell or exosome can be determined using assays (e.g. ExoELISA and rt-PCR reactions) described herein.

Example 3-Co-Detection and Quantitation of Nucleic Acids and Proteins

This example illustrates one example of using the present invention for detecting nucleic acids and proteins using the present integrated droplet microfluidic system.

In this example, a panel of protein markers and gene markers that might be used to detect many solid tumors prior to metastases is evaluated. Diagnosis based on both protein markers and gene markers generally provide a more accurate diagnosis.

A digital PCR assay is designed to simultaneously quantify and assess multiple relevant DNA mutants, or multiple regions of driver genes that are commonly mutated in a variety of cancer types. For downstream confirmation, assay for quantifying relevant cell free protein markers is designed. Droplet digital ELISA can be utilized in conjunction with the present integrated droplet microfluidic system for absolute counting of cell free proteins.

The combined results of the quantity of protein markers and gene markers will likely give a more accurate and sensitive diagnosis than using either type of the markers alone.

Example 4-Co-Detection and Quantitation of Protein and Messenger RNA (mRNA)

This example illustrates using the present invention for the detection of proteins and mRNA.

Integrated co-detection of proteins and mRNAs from the same cell has the potential to not only reveal the correlation between these two classes of biologically important molecules, but also help understand the mechanisms of gene regulation, at both the transcriptional and translational levels.

Procedures described in Example 2 can be applied to this example for the detection and quantitation of mRNA. Procedures described in Example 3 can be applied to this example for the detection and quantification of protein using droplet digital ELISA.

Example 5-Co-Detection and Absolute Counting of DNA, RNA and Protein in an Exosome This example illustrates using the present invention for detecting DNA, RNA and protein from a single exosome.

Exosome contains biomolecules including DNA, RNA and protein within its lumen or on its lipid membrane. These biomolecules can be extracted from an exosome isolated from a serum sample. With the present invention, absolute count of exosome with specific targets can be determined digitally using ExoELISA method, or absolute count of individual biomolecules like DNA, RNA or protein can be determined digitally using digital PCR or digital ELISA. Information about the count of these biomolecules can be coupled or pooled for analysis in the diagnosis of cancer type.

Procedures described in Example 2 can be applied to this example for the detection and quantitation of DNA and RNA from a single exosome, and procedures described in Example 3 can be applied to this example for the detection and quantification of protein using droplet digital ELISA.

REFERENCES

1. P. Zhu and L. Wang, "Passive and active droplet generation with microfluidics: a review" Lab Chip, 2017, 17, 34-75.
2. Baret, Jean-Christophe. "Surfactants in droplet-based microfluidics." Lab on a Chip 12.3 (2012): 422-433.
3. Liu, Chunchen, Xiaonan Xu, Bo Li, Bo Situ, Weilun Pan, Yu Hu, TaixueAn, Shuhuai Yao, and Lei Zheng. "Single-exosome-counting immunoassays for cancer diagnostics." Nano letters (2018).
4. Matthew C. Strain, Steven M. Lada, Tiffany Luong, Steffney E. Rought, Sara Gianella, Valeri H. Terry, Celsa A. Spina, Christopher H. Woelk, and Douglas D. Richman "Highly precise measurement of HIV DNA by droplet digital PCR." PloS one 8.4 (2013): e55943.
5. Baret, Jean-Christophe, et al. "Fluorescence-activated droplet sorting (FADS): efficient microfluidic cell sorting based on enzymatic activity." Lab on a Chip 9.13 (2009): 1850-1858.
6. Cohen, Joshua D., et al. "Combined circulating tumor DNA and protein biomarker-based liquid biopsy for the earlier detection of pancreatic cancers." Proceedings of the National Academy of Sciences 114.38 (2017): 10202-10207.
7. Cohen, Joshua D., et al. "Detection and localization of surgically resectable cancers with a multi-analyte blood test." Science (2018): eaar3247.

8. Xu, X., Yuan, H., Song, R., Yu, M., Chung, H. Y., Hou, Y., Shang, Y., Zhou, H. and Yao, S., 2018. "High aspect ratio induced spontaneous generation of monodisperse picolitre droplets for digital PCR". Biomicrofluidics, 12 (1), p. 014103.
9. Liu, C., Xu, X., Li, B., Situ, B., Pan, W., Hu, Y., An, T., Yao, S. and Zheng, L., 2018. "Single-exosome-counting immunoassays for cancer diagnostics". Nano letters.
10. Cohen, Limor, and David R. Walt. "Single-molecule arrays for protein and nucleic acid analysis." Annual Review of Analytical Chemistry 10 (2017): 345-363.
11. Abbyad, Paul, et al. "Rails and anchors: guiding and trapping droplet microreactors in two dimensions." Lab on a Chip 11.5 (2011): 813-821.
12. Huebner, Ansgar, et al. "Static microdroplet arrays: a microfluidic device for droplet trapping, incubation and release for enzymatic and cell-based assays." Lab on a Chip 9.5 (2009): 692-698.
13. NiveditaMajumdar, Thomas Wessel, Jeffrey Marks, 'Digital PCR Modeling for Maximal Sensitivity, Dynamic Range and Measurement Precision' (2015), PLOS ONE 10(3): e0118833.
14. Chen, Walter W., et al. BEAMing and droplet digital PCR analysis of mutant IDHI mRNA in glioma patient serum and cerebrospinal fluid extracellular vesicles. *Molecular Therapy-Nucleic Acids* 2 (2013).
15. Li, Tianwen, et al. Plasma circular RNA profiling of patients with gastric cancer and their droplet digital RT-PCR detection. *Journal of Molecular Medicine* 96.1 (2018): 85-96.

What we claim are:

1. A method for real-time and digital count of cells or exosomes containing target biomolecules in a sample containing said cells or exosomes, comprising the steps of:
   a) providing to a droplet generator said sample and reagents suitable for said method;
   b) generating droplets with said droplet generator, wherein some droplets contain said reagents and said cells or exosomes;
   c) allowing some of said reagents to lyse said cells or exosomes to release said target biomolecules, and then some of said reagents to label said target biomolecules, producing fluorescent signals;
   d) spreading the droplets in a one-layer configuration in a droplet storage chamber, wherein the droplet storage chamber comprises rows of anchoring structures for anchoring the droplets to pre-determined positions in the droplet storage chamber;
   e) capturing an image of the droplets in the droplet storage chamber by a microscopic camera and detecting fluorescent signals from all droplets.

2. The method of claim 1, wherein in step b) each of said some droplets contains no more than one copy of the target biomolecules of the same type.
3. The method of claim 1, wherein the target biomolecules to be labelled in step c) are of the same type or different types.
4. The method of claim 1, wherein the method detects 1-10 types of target biomolecules.
5. The method of claim 1, wherein said target biomolecules are selected from the group consisting of nucleic acids, peptides, proteins, enzymes, viruses and microorganisms.
6. The method of claim 5, wherein said nucleic acids are selected from the group consisting of coding DNA, non-coding DNA, messenger RNA, ribosomal RNA, micro-RNA and transfer RNA.
7. The method of claim 5, wherein step (e) is performed continuously or intermittently when the target biomolecules are being labelled in step (c).
8. The method of claim 7, wherein the droplets collected are introduced to a droplet sorting unit to select droplets containing a particular type of target biomolecules or having particular properties.
9. The method of claim 1, wherein steps (c), (d) and (e) are performed concurrently to detect fluorescent signals in real time.
10. The method of claim 1, wherein the method further comprises a step of collecting the droplets after any one of steps (c)-(e).
11. The method of claim 1, wherein the droplets collected are disrupted to obtain a suspension comprising labelled target biomolecules.
12. The method of claim 1, wherein the droplet generator comprises a structure selected from the group consisting of a flow focusing structure, a cross flowing structure, a co-flowing structure, a step emulsion structure and a microchannel emulsification structure.
13. The method of claim 1, wherein the sample and reagents are introduced to the droplet generator through the same inlet or different inlets.
14. The method of claim 1, wherein fluorescent signals are detected by a charge-couple device.
15. The method of claim 1, wherein the droplets have a diameter in the range of 5 μm to 200 μm.
16. The method of claim 1, wherein the quantity of droplets generated ranges from several hundreds to several millions.
17. The method of claim 1, wherein the total number of said target biomolecules is indicative of the severity or lack of a disease.

* * * * *